(12) United States Patent
Lynch et al.

(10) Patent No.: US 8,399,409 B2
(45) Date of Patent: *Mar. 19, 2013

(54) COMPOSITIONS AND METHODS FOR ARTHRODETIC PROCEDURES

(75) Inventors: Samuel E. Lynch, Franklin, TN (US); Charles E. Hart, Brentwood, TN (US)

(73) Assignee: BioMimetic Therapeutics Inc., Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/349,413

(22) Filed: Jan. 12, 2012

(65) Prior Publication Data

US 2012/0130435 A1 May 24, 2012

Related U.S. Application Data

(63) Continuation of application No. 12/513,491, filed as application No. PCT/US2007/083638 on Nov. 5, 2007, now Pat. No. 8,106,008.

(60) Provisional application No. 60/856,588, filed on Nov. 3, 2006.

(51) Int. Cl.
*A61K 38/18* (2006.01)
*A61F 2/00* (2006.01)
*A61F 13/00* (2006.01)

(52) U.S. Cl. .......... 514/8.2; 424/422; 424/423; 424/426

(58) Field of Classification Search ........................ None
See application file for complete search history.

(56) References Cited

U.S. PATENT DOCUMENTS

| | | | |
|---|---|---|---|
| 5,124,316 A | 6/1992 | Antoniades et al. | |
| 5,149,691 A | 9/1992 | Rutherford | |
| 5,516,896 A | 5/1996 | Murray et al. | |
| 5,531,794 A | 7/1996 | Takagi et al. | |
| 5,549,123 A | 8/1996 | Okuyama et al. | |
| 6,077,989 A | 6/2000 | Kandel et al. | |
| 6,083,910 A | 7/2000 | Kunitani et al. | |
| 6,136,029 A | 10/2000 | Johnson et al. | |
| 6,180,606 B1 | 1/2001 | Chen et al. | |
| 6,346,123 B1 | 2/2002 | McKay | |
| 6,576,015 B2 | 6/2003 | Geistlich et al. | |
| 6,949,251 B2 | 9/2005 | Dalal et al. | |
| 6,972,130 B1 | 12/2005 | Lee et al. | |
| 7,052,518 B2 | 5/2006 | Irie et al. | |
| 7,357,941 B2 | 4/2008 | Dalal et al. | |
| 7,390,498 B2 | 6/2008 | Dalal et al. | |
| 7,473,678 B2 * | 1/2009 | Lynch ........................... 514/1.1 | |
| 7,491,384 B2 | 2/2009 | Hart et al. | |
| 7,597,883 B2 | 10/2009 | Hart et al. | |
| 7,799,754 B2 * | 9/2010 | Hart et al. ...................... 514/8.2 | |
| 8,106,008 B2 * | 1/2012 | Lynch et al. ................... 514/8.2 | |
| 2002/0018796 A1 | 2/2002 | Wironen | |
| 2002/0022885 A1 | 2/2002 | Ochi | |
| 2002/0098222 A1 | 7/2002 | Wironen et al. | |
| 2003/0049328 A1* | 3/2003 | Dalal et al. .................. 424/602 | |
| 2003/0109537 A1 | 6/2003 | Turner et al. | |
| 2003/0180376 A1 | 9/2003 | Dalal et al. | |
| 2003/0232071 A1 | 12/2003 | Gower et al. | |
| 2004/0064194 A1 | 4/2004 | Irie et al. | |
| 2004/0265350 A1 | 12/2004 | Sambrook et al. | |
| 2005/0027367 A1 | 2/2005 | Heide et al. | |
| 2005/0170012 A1 | 8/2005 | Dalal et al. | |
| 2006/0084602 A1 | 4/2006 | Lynch | |
| 2006/0233853 A1 | 10/2006 | Remington et al. |
| 2006/0292198 A1 | 12/2006 | Dalal et al. |
| 2007/0129807 A1 | 6/2007 | Lynch et al. |
| 2007/0207185 A1 | 9/2007 | Hart et al. |
| 2007/0259814 A1 | 11/2007 | Lynch |
| 2008/0027470 A1 | 1/2008 | Hart et al. |
| 2009/0074753 A1 | 3/2009 | Lynch |
| 2009/0232890 A1 | 9/2009 | Lynch et al. |
| 2010/0151025 A1 | 6/2010 | Lynch et al. |
| 2010/0174368 A1 | 7/2010 | Lynch et al. |
| 2010/0183515 A1 | 7/2010 | Hart et al. |
| 2010/0196347 A1 | 8/2010 | Kery et al. |
| 2010/0247651 A1 | 9/2010 | Kestler et al. |

FOREIGN PATENT DOCUMENTS

| | | |
|---|---|---|
| EP | 1719531 | 11/2006 |
| EP | 1719532 | 11/2006 |
| GB | 2367497 | 4/2002 |
| WO | 8803409 | 5/1988 |
| WO | 9422463 | 10/1994 |
| WO | 9528950 | 11/1995 |
| WO | 9840113 | 9/1998 |
| WO | 9967289 | 12/1999 |
| WO | 0004940 | 2/2000 |
| WO | 02070029 | 9/2002 |
| WO | 03006025 | 1/2003 |
| WO | 03071991 | 9/2003 |
| WO | 2005032461 | 4/2005 |
| WO | 2006044334 | 4/2006 |
| WO | 2007061889 | 5/2007 |
| WO | 2007089997 | 8/2007 |
| WO | 2007092622 | 8/2007 |
| WO | 2008005427 | 1/2008 |
| WO | 2008073628 | 6/2008 |
| WO | 2008103690 | 8/2008 |
| WO | 2008151193 | 12/2008 |
| WO | 2009100454 | 8/2009 |
| WO | 2010030714 | 3/2010 |
| WO | 2010071857 | 6/2010 |
| WO | 2010102266 | 9/2010 |

OTHER PUBLICATIONS

Hee H. T., et al. "Do autologous growth factors enhance transforaminal lumbar interbody fusion?" European Spine Journal 200308 DE, vol. 12, No. 4, Aug. 2003, pp. 400-407. Bateman, J. et al. "Platelet-Derived Growth Factor Enhancement of Two Alloplastic Bone Matrices," J. Periodontol. (Nov. 2005) 76(11):1833-1841.
Canalis, "Effect of Growth Factors on Bone Cell Replication and Differentiation," Clinical Orthopedics and Related Research, Mar. 1985, 193:246-263.
Collins, T. et al. (Aug. 22, 1985). "Cultured Human Endothelial Cells Express Platelet-Derived Growth Factor B Chain: cDNA Cloninq and Structural Analysis," Nature 316:748-750.
Hollinger, J.O. et al. (Feb. 2008). "Recombinant Human Platelet Derived Growth Factor: Bloloov and Clinical Applications," J. Bone & Joint Suraerv so-Arsuool. 1) :48-54.
Mitlak et al. "The Effect of Systemically Administered PDGF-BB on the Rodent Skeleton," Journal of Bone and Mineral Research, 1996, 11 (2):238-247.

* cited by examiner

*Primary Examiner* — Marianne P Allen
(74) *Attorney, Agent, or Firm* — Waddey & Patterson P.C.; James R. Cartiglia; Hilary Dorr Lang

(57) ABSTRACT

The present invention provides compositions and methods for facilitating fusion of bones in a joint. The present invention provides compositions and methods for promoting fusion of bones in arthrodetic procedures. In one embodiment, a method of performing an arthrodetic procedure comprises providing a composition comprising PDGF disposed in a biocompatible matrix and applying the composition to a site of desired bone fusion in a joint.

55 Claims, No Drawings

COMPOSITIONS AND METHODS FOR ARTHRODETIC PROCEDURES

CROSS-REFERENCE TO RELATED APPLICATIONS

This application is a continuation of U.S. patent application Ser. No. 12/513,491, filed Feb. 23, 2010, now U.S. Pat. No. 8,106,008, which is a national phase filing under 35 U.S.C. §371 of International Application No. PCT/US2007/083638, filed Nov. 5, 2007, which claims the benefit of the filing date of U.S. Provisional Patent Application No. 60/856,588, filed Nov. 3, 2006, the entire contents of which is are incorporated herein by reference.

FIELD OF THE INVENTION

The present invention relates to compositions and methods useful for arthrodetic procedures and for promoting fusion of bones in a joint.

BACKGROUND OF THE INVENTION

Musculoskeletal problems are pervasive throughout the population in all age groups and in both sexes. Half of Americans will need services for fractures or bone fusions at some point in their lifetime according to a widely published article presented at the 2003 annual meeting of the American Academy of Orthopedic Surgeons (AAOS). More than $10 billion per year is spent in the United States on hospital care associated with fracture treatment according to this article.

In many cases, arthrodetic procedures are used to treat musculoskeletal problems associated with various joints of patients. Arthrodetic procedures and arthrodesis, as used herein, refer to the surgical immobilization of a joint resulting from fusion of bones of the joint. Arthrodesis of the foot and ankle is a commonly utilized procedure for the treatment of multiple etiologies of foot and ankle pathology, including post-traumatic arthritis, inflammatory arthropathy, seronegative arthropathy, significant joint instability, suboptimal alignment and/or pain. Midfoot, hindfoot, and ankle fusion procedures, such as the triple (three hindfoot articulations), subtalar, talonavicular, and ankle fusions involve the treatment principles of taking down any residual cartilage to the subchondral surface at the level of the involved joint without disturbing its anatomy, stabilizing the joint thereafter with rigid fixation, placing autograft bone (harvested locally or from iliac crest) or other appropriate fusion preparation into surrounding interstices and defects across the joint surface, followed by a relatively standard post-operative regimen of short term immobilization, physical therapy, and gradually increasing load on the fusion site(s).

The time to healing after fusion procedures is longer than that after more conservative treatment methods due to the time required for fusion/union. Historically, an average of two to three months are needed to achieve complete bony union and full weight bearing (FWB) status after these operations. Nonunion rates of other midfoot, hindfoot, and ankle fusion procedures (0-40%) may be higher than those cited for the forefoot. The literature consensus on non-union rates associated with foot and ankle procedures is approximately 10% (See, e.g., Easley et al., Isolated Subtalar Arthrodesis, JBJS, 82-A(5), 2000 pp. 613-624). Nonunions will be detected by 4 and 8 months radiographically and are generally clinically well established by 6-9 months (hence the clinically accepted standard of 4-5 months without evidence of bony progression to declare delayed union and 9 months for declaring nonunion).

Arthrodetic procedures, including arthrodesis of the foot and ankle, often utilize autologous bone grafts to facilitate sufficient bone healing. Autologous bone grafts are widely used due to the fact that there is no risk of cross-contamination associated with allografts or xenografts. Clinical difficulties, nevertheless, exist with autologous bone grafts. Most of these difficulties result from the harvest of the bone graft, including increased operative time, hospital stay and cost, increased blood loss, post-operative pain, risk of infection and/or fracture. Other reported complications associated with autograft include a potential nidus for infection associated with avascular bone, limited tissue supply, and variability in cellular activity of the bone graft (See e.g., Morbidity at bone graft donor sites, J Orthop Trauma 1989, 3, pp. 192-195). In addition to these complications, there is a limited amount of bone graft that may be harvested for use as a bone void filler.

In view of the difficulties associated with autologous bone grafts, it would be desirable to provide alternative osteogenic regeneration systems. It would additionally be desirable to provide methods of using alternative osteogenic regeneration systems in bone fracture treatments and arthrodetic procedures, including foot and ankle arthrodesis.

SUMMARY

The present invention provides compositions and methods for use in arthrodetic procedures. These compositions and methods promote fusion of bones in a joint. In accordance with embodiments of the present invention, there are provided compositions and methods for use in arthrodetic procedures, such as arthrodetic procedures of the foot and ankle. The present compositions and methods facilitate the healing response in arthrodetic procedures including bony union at fusion sites.

The present invention additionally provides for the use of compositions of the present invention in the preparation of an implant material useful for the fusion of bones in a joint. The present invention additionally provides for the use of compositions of the present invention in the preparation of a medicament useful for the fusion of bones in a joint.

In one aspect, a composition provided by the present invention for promoting the fusion of bone in an arthrodetic procedure comprises a solution comprising platelet derived growth factor (PDGF) and a biocompatible matrix, wherein the solution is disposed or incorporated in the biocompatible matrix. In some embodiments, the PDGF is absorbed by the biocompatible matrix. In other embodiments, the PDGF is adsorbed onto one or more surfaces of the biocompatible matrix. In a further embodiment, the PDGF is absorbed by the biocompatible matrix and adsorbed onto surfaces of the biocompatible matrix.

In some embodiments, PDGF is present in the solution in a concentration ranging from about 0.01 mg/ml to about 10 mg/ml, from about 0.05 mg/ml to about 5 mg/ml, from about 0.1 mg/ml to about 1.0 mg/ml or from about 0.2 mg/ml to about 0.4 mg/ml. The concentration of PDGF within the solution may be within any of the concentration ranges stated above.

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as rhPDGF-BB.

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of intact rhPDGF-B (1-109).

The present invention provides a composition for promoting the fusion of two or more bones in an arthrodetic procedure comprising a PDGF solution disposed in a biocompatible matrix, wherein the biocompatible matrix comprises a bone substituting agent (also called a bone scaffolding material herein) and optionally a biocompatible binder. Exemplary bone substituting agents include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, or demineralized bone (e.g., demineralized freeze-dried cortical or cancellous bone)). The PDGF solution may have any concentration of PDGF as described herein. A bone scaffolding material, in some embodiments, comprises calcium phosphate. In one embodiment, calcium phosphate comprises β-TCP. In some embodiments, biocompatible matrices may include calcium phosphate particles with or without biocompatible binders or bone allograft such as demineralized freeze dried bone allograft (DFDBA) or particulate demineralized bone matrix (DBM). In another embodiment, biocompatible matrices may include bone allograft such as DFDBA or DBM.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises hyaluronic acid.

In another aspect, the present invention provides a kit for use in arthrodetic procedures comprising a biocompatible matrix in a first package and a solution comprising PDGF in a second package. In some embodiments, the solution comprises a predetermined concentration of PDGF. The concentration of the PDGF can be predetermined according to requirements of the arthrodetic procedure(s) being performed. Moreover, in some embodiments, the biocompatible matrix can be present in the kit in a predetermined amount. In some embodiments, the biocompatible matrix in the kit comprises a bone scaffolding material, a bone scaffolding material and a biocompatible binder, and/or bone allograft such as DFDBA or particulate DBM. In one embodiment, the bone scaffolding material comprises a calcium phosphate, such as β-TCP. In one embodiment, the binder comprises collagen. The amount of biocompatible matrix provided by a kit relates to requirements of the arthrodetic procedure(s) being performed. In some embodiments, the second package containing the PDGF solution comprises a syringe. A syringe can facilitate disposition of the PDGF solution in or on the biocompatible matrix for application at a surgical site, such as a site of bone fusion in an arthrodetic procedure. In some embodiments, once the PDGF solution has been incorporated into the biocompatible matrix, the resulting composition is placed in a second syringe and/or cannula for delivery to a site of desired bone fusion in a joint. Alternatively, the composition may be applied to the desired site with another application means, such as a spatula, spoon, knife, or equivalent device.

The present invention additionally provides methods for producing compositions for use in arthrodetic procedures as well as methods of performing arthrodetic procedures. In one embodiment, a method for producing a composition comprises providing a solution comprising PDGF, providing a biocompatible matrix, and disposing or incorporating the PDGF solution in the biocompatible matrix.

In another embodiment, a method of performing an arthrodetic procedure comprises providing a composition comprising a PDGF solution disposed in a biocompatible matrix and applying the composition to a site of desired bone fusion in a joint. In some embodiments, a method of performing an arthrodetic procedure comprises applying the composition to at least one site of desired bone fusion in a plurality of joints. Applying the composition to a site of desired bone fusion, in some embodiments, comprises injecting the composition in the site of desired bone fusion.

In some embodiments, a method of performing an arthrodetic procedure comprises surgically accessing a site of desired bone fusion in a joint, incorporating a composition comprising a PDGF solution disposed in a biocompatible matrix, applying the composition into the site of desired bone fusion, suturing soft tissues over the composition, and permitting cellular migration and infiltration into the composition for subsequent formation of bone.

In some embodiments, an arthrodetic procedure comprises subtalar arthrodesis. In other embodiments, an arthrodetic procedure comprises talonavicular arthrodesis. In another embodiment, an arthrodetic procedure comprises triple arthrodesis. In some embodiments, an arthrodetic procedure comprises a calcaneocuboid arthrodesis. In a further embodiment, an arthrodetic procedure comprises an ankle arthrodesis.

In some embodiments, an arthrodetic procedure comprises a mid-foot fusion (the first, second, third or all 3 medial tarsometatarsal (TMT) joints). In other embodiments, an arthrodetic procedure comprises a naviculocuneiform (NC) joint fusion. In another embodiment, an arthrodetic procedure comprises a first metatarsophalangeal (MP) joint fusion. In a further embodiment, an arthrodetic procedure comprises an interphalangeal joint fusion procedure.

Accordingly, it is an object of the present invention to provide compositions comprising PDGF incorporated in a biocompatible matrix wherein the compositions are useful in facilitating the fusion of bones in arthrodetic procedures.

Another object of the present invention is to provide arthrodetic procedures using a composition comprising PDGF in a biocompatible matrix.

It is another object of the present invention to provide a composition comprising PDGF incorporated in a matrix and a method of using this composition to facilitate bone graft formation in arthrodetic procedures.

Another object of the present invention is to provide compositions comprising PDGF incorporated in a matrix which serve as alternatives to autologous bone grafts in arthrodetic procedures.

A further object of the present invention is to accelerate healing associated with bone fusion in arthrodetic procedures.

These and other embodiments of the present invention are described in greater detail in the description which follows. These and other objects, features, and advantages of the present invention will become apparent after review of the following detailed description of the disclosed embodiments and claims.

DETAILED DESCRIPTION

The present invention provides for the use of compositions of the present invention for use in arthrodetic procedures. The present invention additionally provides for the use of compositions of the present invention in the preparation of an implant material useful for the fusion of bones in a joint. The present invention additionally provides for the use of compositions of the present invention in the preparation of a medicament useful for the fusion of bones in a joint.

The present invention provides compositions and methods for promoting the fusion of bone in arthrodetic procedures, including arthrodetic procedures of the foot and ankle. In one embodiment, a composition for promoting bone fusion in an arthrodetic procedure comprises a solution comprising PDGF and a biocompatible matrix, wherein the solution is disposed or incorporated in the biocompatible matrix. In another embodiment, a composition comprises a PDGF solution disposed in a biocompatible matrix, wherein the biocompatible matrix comprises a bone scaffolding material and a biocompatible binder.

In some embodiments, the PDGF is absorbed by the biocompatible matrix. In other embodiments, the PDGF is adsorbed onto one or more surfaces of the biocompatible matrix. In a further embodiment, the PDGF is absorbed by the biocompatible matrix and adsorbed onto surfaces of the biocompatible matrix.

The present invention also provides a kit comprising a biocompatible matrix in a first package and a solution comprising PDGF in a second package. In some embodiments, the solution comprises a predetermined concentration of PDGF. In some embodiments, the concentration of PDGF is consistent with the values provided herein. The concentration of the PDGF can be predetermined according to the arthrodetic procedure(s) being performed. Moreover, in some embodiments, the biocompatible matrix can be present in the kit in a predetermined amount. The biocompatible matrix may optionally contain a biocompatible binder, or the binder may be provided in a third package in the kit. The amount of biocompatible matrix provided by a kit can be dependent on the arthrodetic procedure(s) being performed. In some embodiments, the second package containing the PDGF solution comprises a syringe. A syringe can facilitate disposition of the PDGF solution in the biocompatible matrix for application at a surgical site, such as a site of bone fusion in an arthrodetic procedure.

Turning now to components that can be included in various embodiments of the present invention, compositions of the present invention comprise a solution comprising PDGF.

PDGF Solutions

In one aspect, a composition for arthrodetic procedures provided by the present invention comprises a solution comprising PDGF and a biocompatible matrix, wherein the solution is disposed or incorporated in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges, including the upper limit and lower limit of each range. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml; about 0.55 mg/ml; about 0.6 mg/ml; about 0.65 mg/ml; about 0.7 mg/ml; about 0.75 mg/ml; about 0.8 mg/ml; about 0.85 mg/ml; about 0.9 mg/ml; about 0.95 mg/ml; or about 1.0 mg/ml. It is to be understood that these concentrations are simply examples of particular embodiments, and that the concentration of PDGF may be within any of the concentration ranges stated above, including the upper limit and lower limit of each range.

Various amounts of PDGF may be used in the compositions of the present invention. Amounts of PDGF that are used, in some embodiments, include amounts in the following ranges: about 1 μg to about 50 mg, about 10 μg to about 25 mg, about 100 μg to about 10 mg, or about 250 μg to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, incorporated herein by reference, or any other assay known in the art for determining PDGF concentration. When provided herein, the molar concentration of PDGF is determined based on the molecular weight (MW) of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF, such as rhPDGF-BB.

PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthetic. When obtained from natural sources, PDGF can be derived from biological fluids. Biological fluids, according to some embodiments, can comprise any treated or untreated fluid associated with living organisms including blood Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When PDGF is produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available GMP recombinant PDGF-BB can be obtained commercially from Chiron Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with one embodiment, the rhPDGF-BB comprises at least 65% of intact rhPDGF-B (1-109). In another embodiment, the rhPDGF-BB comprises at least 75%, 80%, 85%, 90%, 95%, or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In one embodiment, sodium acetate buffer is used. The buffers can be employed at different molarities, for example, about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, from about 5.5 to about 7.0, or from about 5.5 to about 6.5, or any value within these ranges. The pH of solutions comprising PDGF, in some embodiments, can be compatible with the prolonged stability and efficacy of PDGF or any other desired biologically active agent. PDGF may be more stable in an acidic environment. Therefore, in accordance with one embodiment, the present invention comprises an acidic storage formulation of a PDGF solution. In accordance with this embodiment, the PDGF solution preferably has a pH from about 3.0 to about 7.0 or from about 4.0 to about 6.0. The biological activity of PDGF, however, can be optimized in a solution having a neutral pH range. Therefore, in a further embodiment, the present invention comprises a neutral pH formulation of a PDGF solution. In accordance with this embodiment, the PDGF solution has a pH from about 5.0 to about 8.0, from about 5.5 to about 7.0, or from about 5.5 to about 6.5. In accordance with a method of the present invention, an acidic PDGF solution is reformulated to a neutral pH composition, wherein such composition is then used to fuse bones in a joint. In accordance with a preferred embodiment of the present invention, the PDGF utilized in the solutions is rh-PDGF-BB. In a further embodiment, the pH of the PDGF containing solution can be altered to optimize the binding kinetics of PDGF to a biocompatible matrix.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N, N,N', N'-tetraacetic acid (EGTA), aprotinin, ε-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to incorporate the PDGF solutions. The compositions may also comprise a biocompatible binder either with or without addition of a biocompatible matrix.

Biocompatible Matrix

In another embodiment of all aspects of the invention, the biocompatible matrix of the implant material is, or additionally includes, one or more bone substituting agents. In another embodiment of all aspects of the invention, the biocompatible matrix of the implant material is, or additionally includes, one or more bone scaffolding material or bone substituting agent and further comprises a biocompatible binder.

Bone Scaffolding Material

A biocompatible matrix, according to embodiments of the present invention, comprises a bone scaffolding material. It is to be understood that the terms bone scaffolding material and bone substituting agent are used interchangeably in this patent application. The bone scaffolding material provides the framework or scaffold for new bone and tissue growth to occur. A bone substituting agent is one that can be used to permanently or temporarily replace bone. Following implantation, the bone substituting agent can be retained by the body or it can be resorbed by the body and replaced with bone. Exemplary bone substituting agents include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, mineralized bone, mineralized bone allograft, mineralized deproteinized xenograft, or demineralized bone (e.g., demineralized freeze-dried cortical or cancellous bone)). In an embodiment, the carrier substance is bioresorbable. A bone scaffolding material, in some embodiments, comprises at least one calcium phosphate. In other embodiments, a bone scaffolding material comprises a plurality of calcium phosphates. Calcium phosphates suitable for use as a bone scaffolding material, in embodiments of the present invention, have a calcium to phosphorus atomic ratio ranging from 0.5 to 2.0. In some embodiment, a biocompatible matrix comprises an allograft such as DFDBA or particulate DBM.

Non-limiting examples of calcium phosphates suitable for use as bone scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxapatite, tetracalcium phosphate (TTCP), heptacalcium decaphosphate, calcium metaphosphate, calcium pyrophosphate dihydrate, calcium pyrophosphate, carbonated calcium phosphate, or mixtures thereof.

In another embodiment, the bone substituting agent has a porous composition. Porosity is a desirable characteristic as it facilitates cell migration and infiltration into the implant material so that the infiltrating cells can secrete extracellular bone matrix. Porosity also provides access for vascularization. Porosity also provides a high surface area for enhanced resorption and release of active substances, as well as increased cell-matrix interaction. The composition can be provided in a shape suitable for implantation (e.g., a sphere, a cylinder, or a block) or it can be sized and shaped prior to use. In a preferred embodiment, the bone substituting agent is a calcium phosphate (e.g., β-TCP). Porous bone scaffolding materials, according to some embodiments, can comprise pores having diameters ranging from about 1 μm to about 1 mm. In one embodiment, a bone scaffolding material comprises macropores having diameters ranging from about 100 μm to about 1 mm. In another embodiment, a bone scaffolding material comprises mesopores having diameters ranging from about 10 μm to about 100 μm. In a further embodiment, a bone scaffolding material comprises micropores having diameters less than about 10 μm. Embodiments of the present invention contemplate bone scaffolding materials comprising macropores, mesopores, and micropores or any combination thereof.

A porous bone scaffolding material, in one embodiment, has a porosity greater than about 25% or greater than about 40%. In another embodiment, a porous bone scaffolding material has a porosity greater than about 50%, greater than about 60%, greater than about 65%, greater than about 70%, greater than about 80%, or greater than about 85%. In a further embodiment, a porous bone scaffolding material has a porosity greater than about 90%. In some embodiments, a porous bone scaffolding material comprises a porosity that facilitates cell migration into the scaffolding material.

In some embodiments, a bone scaffolding material comprises a plurality of particles. A bone scaffolding material, for example, can comprise a plurality of calcium phosphate particles. Particles of a bone scaffolding material, in some embodiments, can individually demonstrate any of the pore diameters and porosities provided herein for the bone scaffolding. In other embodiments, particles of a bone scaffolding material can form an association to produce a matrix having any of the pore diameters or porosities provided herein for the bone scaffolding material.

Bone scaffolding particles may be mm, μm or submicron (nm) in size. Bone scaffolding particles, in one embodiment, have an average diameter ranging from about 1 μm to about 5 mm. In other embodiments, particles have an average diameter ranging from about 1 mm to about 2 mm, from about 1 mm to about 3 mm, or from about 250 μm to about 750 μm. Bone scaffolding particles, in another embodiment, have an average diameter ranging from about 100 μm to about 300 μm. In a further embodiment, the particles have an average diameter ranging from about 75 μm to about 300 μm. In additional embodiments, bone scaffolding particles have an average diameter less than about 25 μm, less than about 1 μm and, in some cases, less than about 1 mm. In some embodiments, a bone scaffolding particles have an average diameter ranging from about 100 μm to about 5 mm or from about 100 μm to about 3 mm. In other embodiments, bone scaffolding particles have an average diameter ranging from about 250 μm to about 2 mm, from about 250 μm to about 1 mm, from about 200 μm to about 3 mm. Particles may also be in the range of about 1 nm to about 1000 nm, less than about 500 nm or less than about 250 nm.

Bone scaffolding materials, according to some embodiments, can be provided in a shape suitable for implantation (e.g., a sphere, a cylinder, or a block). In other embodiments, bone scaffolding materials are moldable, extrudable, and/or injectable. Moldable, extrudable, and/or injectable bone scaffolding materials can facilitate efficient placement of compositions of the present invention in and around target sites in bone and between bones at sites of desired bone fusion during arthrodetic procedures. In some embodiments, moldable bone scaffolding materials can be applied to sites of bone fusion with a spatula or equivalent device. In some embodiments, bone scaffolding materials are flowable. Flowable bone scaffolding materials, in some embodiments, can be applied to sites of bone fusion through a syringe and needle or cannula. In some embodiments, bone scaffolding materials harden in vivo.

In some embodiments, bone scaffolding materials are bioresorbable. A bone scaffolding material, in one embodiment, can be at least 30%, 40%, 50%, 60%, 70%, 75% or 90% resorbed within one year subsequent to in vivo implantation. In another embodiment, a bone scaffolding material can be resorbed at least 5%, 10%, 20%, 30%, 40%, 50%, 60%, 70%, 75% or 90% within 1, 3, 6, 9, 12, or 18 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Bone Scaffolding Comprising β-Tricalcium Phosphate

In one embodiment, a bone scaffolding material for use as a biocompatible matrix can comprise β-TCP. β-TCP, according to some embodiments, can comprise a porous structure having multidirectional and interconnected pores of varying diameters. In some embodiments, β-TCP comprises a plurality of pockets and non-interconnected pores of various diameters in addition to the interconnected pores. The porous structure of β-TCP, in one embodiment, comprises macropores having diameters ranging from about 100 μm to about 1 mm, mesopores having diameters ranging from about 10 μm to about 100 μm, and micropores having diameters less than about 10 μm. Macropores and micropores of the β-TCP can facilitate osteoinduction and osteoconduction while macropores, mesopores and micropores can permit fluid communication and nutrient transport to support bone regrowth throughout the β-TCP biocompatible matrix.

In comprising a porous structure, β-TCP, in some embodiments, can have a porosity greater than 25% or greater than about 40%. In other embodiments, β-TCP can have a porosity greater than 50%, greater than about 60%, greater than about 65%, greater than about 70%, greater than about 75%, greater than about 80%, or greater than about 85%. In a further embodiment, β-TCP can have a porosity greater than 90%. In some embodiments, β-TCP can have a porosity that facilitates cell migration into the β-TCP.

In some embodiments, a bone scaffolding material comprises β-TCP particles. B-TCP particles, in some embodiments, can individually demonstrate any of the pore diameters and porosities provided herein for β-TCP. In other embodiments, β-TCP particles of a bone scaffolding material can form an association to produce a matrix having any of the pore diameters or porosities provided herein for the bone scaffolding material. Porosity facilitates cell migration and infiltration into the matrix for subsequent bone formation.

β-TCP particles, in one embodiment, have an average diameter ranging from about 1 μm to about 5 mm. In other embodiments, β-TCP particles have an average diameter ranging from about 1 mm to about 2 mm, from about 1 mm to about 3 mm, from about 250 μm to about 750 μm, from about 250 μm to about 1 mm, from about 250 μm to about 2 mm, or from about 200 μm to about 3 mm. In another embodiment, β-TCP particles have an average diameter ranging from about 100 μm to about 300 μm. In a further embodiment, β-TCP particles have an average diameter ranging from about 75 μm to about 300 μm. In additional embodiments, (β-TCP particles have an average diameter less than about 25 μm, average diameter less than about 1 μm, or less than about 1 mm. In some embodiments, β-TCP particles have an average diameter ranging from about 100 μm to about 5 mm or from about 100 μm to about 3 mm.

A biocompatible matrix comprising β-TCP particles, in some embodiments, can be provided in a shape suitable for implantation (e.g., a sphere, a cylinder, or a block). In other embodiments, a β-TCP bone scaffolding material can be moldable, extrudable, and/or injectable thereby facilitating placement of the matrix in and around target sites of desired bone fusion during arthrodetic procedures, such as those in the foot and/or ankle. Flowable matrices may be applied through syringes, tubes, or spatulas or equivalent devices. Flowable β-TCP bone scaffolding materials, in some embodiments, can be applied to sites of bone fusion through a syringe and needle or cannula. In some embodiments, β-TCP bone scaffolding materials harden in vivo.

A β-TCP bone scaffolding material, according to some embodiments, is bioresorbable. In one embodiment, a β-TCP bone scaffolding material can be at least 30%, 40%, 50%, 60%, 65%, 70%, 75%, 80%, or 85% resorbed one year subsequent to in vivo implantation. In another embodiment, a β-TCP bone scaffolding material can be greater than 90% resorbed one year subsequent to in vivo implantation.

Bone Scaffolding Material and Biocompatible Binder

In another embodiment, a biocompatible matrix comprises a bone scaffolding material and a biocompatible binder. Bone scaffolding materials in embodiments of a biocompatible matrix further comprising a biocompatible binder are consistent with those provided hereinabove.

Biocompatible binders, according to some embodiments, can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material and a binder if such material acts to promote cohesion between the combined substances and provides a framework for new bone growth to occur.

Biocompatible binders, in some embodiments, can comprise collagen, polysaccharides, nucleic acids, carbohydrates, proteins, polypeptides, poly(α-hydroxy acids), poly (lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly (L-lactide) (PLLA), poly(D,L-lactide) (PDLLA), polyglycolide (PGA), poly(lactide-co-glycolide) (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, lecithin, N,O-carboxymethyl chitosan, phosphatidylcholine derivatives, a dextran (e.g., α-cyclodextrin, β-cyclodextrin, γ-cyclodextrin, or sodium dextran sulfate), fibrin glue, lecithin, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, a pluronic acid, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix.

Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 1 weight percent to about 70 weight percent, about 5 weight percent to about 50 weight percent, about 10 weight percent to about 40 weight percent, about 15 weight percent to about 35 weight percent, or about 15 weight percent to about 25 weight percent of the biocompatible matrix. In a further embodiment, a biocompatible binder can be present in an amount of about 20 weight percent of the biocompatible matrix.

A biocompatible matrix comprising a bone scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a bone scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a bone scaffolding material and a biocompatible binder, in some embodiments, can also be provided in a predetermined shape including a block, sphere, or cylinder or any desired shape, for example a shape defined by a mold or a site of application.

A biocompatible matrix comprising a bone scaffolding material and a biocompatible binder, in some embodiments, is bioresorbable as described above. A biocompatible matrix, in such embodiments, can be resorbed within one year of in vivo implantation. In another embodiment, a biocompatible matrix comprising a bone scaffolding material and a biocompatible binder can be resorbed within 1, 3, 6, or 9 months of in vivo implantation. Bioresorbablity will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP bone scaffolding material and a biocompatible collagen binder. β-TCP bone scaffolding materials suitable for combination with a collagen binder are consistent with those provided hereinabove.

A collagen binder, in some embodiments, can comprise any type of collagen, including Type I, Type II, and Type III collagens. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. β-TCP particles suitable for use with a collagen binder can comprise any of the β-TCP particles described herein. In one embodiment, β-TCP particles suitable for combination with a collagen binder have an average diameter ranging from about 1 μm to about 5 mm. In another embodiment, β-TCP particles suitable for combination with a collagen binder have an average diameter ranging from about 1 μm to about 1 mm, from about 1 mm to about 2 mm, from about 1 mm to about 3 mm, from about 250 μm to about 750 μm, from about 250 μm to about 1 mm, from about 250 μm to about 2 mm, from about 200 μm to about 1 mm, or from about 200 μm to about 3 mm. β-TCP particles, in other embodiments, have an average diameter ranging from about 100 μm to about 300 μm. In a further embodiment, β-TCP particles suitable for combination with a collagen binder have an average diameter ranging from about 75 μm to about 300 μm. In additional embodiments, β-TCP particles suitable for combination with a collagen binder have an average diameter less than about 25 μm and, less than about 1 mm or less than about 1 μm. In some embodiments, β-TCP particles suitable for combination with a collagen binder have an average diameter ranging from about 100 μm to about 5 mm or from about 100 μm to about 3 mm.

β-TCP particles, in some embodiments, can be adhered to one another by the collagen binder so as to produce a biocompatible matrix having a porous structure. In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm, mesopores having diameters ranging from about 10 μm to 100 μm, and micropores having diameters less than about 10 μm.

A biocompatible matrix comprising β-TCP particles and a collagen binder can have a porosity greater than about 25% or greater than 40%. In another embodiment, the biocompatible matrix can have a porosity greater than about 50%, greater than about 60%, greater than about 65%, greater than about 70%, greater than about 80%, or greater than about 85%. In a further embodiment, the biocompatible matrix can have a porosity greater than about 90%. Porosity facilitates cell migration and infiltration into the matrix for subsequent bone formation.

A biocompatible matrix comprising β-TCP particles, in some embodiments, can comprise a collagen binder in an amount ranging from about 1 weight percent to about 70 weight percent, from about 5 weight percent to about 50 weight percent, from about 10 weight percent to about 40 weight percent, from about 15 weight percent to about 35 weight percent, or from about 15 weight percent to about 25 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 30%, 40%, 50%, 60%, 70%, 75%, or 90% resorbed one year subsequent to in vivo implantation. In another embodiment, this matrix can be resorbed at least 5%, 10%, 20%, 30%, 40%, 50%, 60%, 70%, 75% or 90% within 1, 3, 6, 9, 12, or 18 months subsequent to in vivo implantation.

A solution comprising PDGF can be disposed in a biocompatible matrix to produce a composition for promoting bone fusion in arthrodetic procedures according to embodiments of the present invention.

Incorporating PDGF Solution in a Biocompatible Matrix

The present invention provides methods for producing compositions for use in arthrodetic procedures. In one embodiment, a method for producing a composition for promoting the fusion of bone comprises providing a solution comprising PDGF, providing a biocompatible matrix, and incorporating the solution in the biocompatible matrix. PDGF solutions and biocompatible matrices suitable for combination are consistent with those described hereinabove.

In one embodiment, a PDGF solution can be incorporated in a biocompatible matrix by soaking the biocompatible matrix in the PDGF solution. A PDGF solution, in another embodiment, can be incorporated in a biocompatible matrix by injecting the biocompatible matrix with the PDGF solution. In some embodiments, injecting a PDGF solution can comprise incorporating the PDGF solution in a syringe and expelling the PDGF solution into the biocompatible matrix to saturate the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can already demonstrate a flowable paste or putty form prior to receiving a solution comprising PDGF.

Compositions Further Comprising Biologically Active Agents

The compositions described herein for promoting and/or facilitating bone fusion in arthrodetic procedures, according to some embodiments, can further comprise one or more biologically active agents in addition to PDGF. Biologically active agents that can be incorporated into compositions of the present invention in addition to PDGF can comprise organic molecules, inorganic materials, proteins, peptides, nucleic acids (e.g., genes, gene fragments, small insert ribonucleic acids [si-RNAs], gene regulatory sequences, nuclear transcriptional factors, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). In some embodiments, biologically active compounds that can be incorporated into compositions of the present invention include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, calcitonin mimetics, statins, statin derivatives, or parathyroid hormone. Preferred factors also include protease inhibitors, as well as osteoporotic treatments that decrease bone resorption including bisphosphonates, and antibodies to receptor activator of NF-kB ligand (RANK) ligand.

Standard protocols and regimens for delivery of additional biologically active agents are known in the art. Additional biologically active agents can be introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition for promoting bone fusion in arthrodetic procedures, according to some embodiments, can further comprise the addition of other bone grafting materials with PDGF including autologous bone marrow, autologous platelet extracts, and synthetic bone matrix materials.

Methods of Performing Arthrodetic Procedures

The present invention also provides methods of performing arthrodetic procedures. In one embodiment, a method of performing an arthrodetic procedure comprises providing a composition comprising a PDGF solution incorporated in a biocompatible matrix and applying the composition to a site of desired bone fusion in a joint. In some embodiments, a method of performing an arthrodetic procedure comprises applying the composition to a site of desired bone fusion in a plurality of joints. A composition comprising a PDGF solution incorporated in a biocompatible matrix, for example, can be packed into a site of desired bone fusion in a joint. In some embodiments, the composition can be packed such that the composition is in contact with the entire surface area of the bones to be fused in the joint. The composition may additionally be applied to the vicinity of the bone fusion site to further strengthen the fused joint.

Bones in any joint may be fused using the compositions and methods of the present invention. Such joints include, but are not limited to joints of the foot, toes, ankle, knee, hip, spine, rib, sternum, clavicle, joint, shoulder, scapula, elbow, wrist, hand, fingers, jaw and skull.

In some embodiments, a method of performing an arthrodetic procedure further comprises aligning the joint and inserting at least one fixation device, such as a screw, into at least one bone of the joint. In some embodiments, a plurality of screws are inserted into at least one bone of the joint.

In another embodiment, a method of the present invention comprises accelerating bony union in an arthrodetic procedure wherein accelerating bony union comprises providing a composition comprising a PDGF solution disposed in a biocompatible matrix and applying the composition to at least one site of bone fusion in a joint.

It is to be understood that the present invention may apply to any desired site for arthrodesis in the appendicular or spinal skeleton.

In one embodiment of the present invention, arthrodetic procedures comprise arthrodesis of the foot and ankle including subtalar arthrodesis, talonavicular arthrodesis, triple arthrodesis, and ankle arthrodesis. Example 3 describes a study designed to demonstrate the efficacy of compositions and methods of the present invention for promoting bone fusion in arthrodetic procedures of the foot and ankle.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of a Composition Comprising a Solution of PDGF and a Biocompatible Matrix A composition comprising a solution of PDGF and a biocompatible matrix of β-TCP was prepared according to the following procedure. The β-TCP comprised β-TCP particles having an average diameter ranging from about 1000 μm to about 2000 μm.

A solution comprising rhPDGF-BB was obtained. rhPDGF-BB is commercially available from Chiron Corporation at a stock concentration of 10 mg/ml (i.e., Lot # QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention, including 1.0 mg/ml.

A ratio of about 3 ml of rhPDGF-BB solution to about 1 g dry weight of the β-TCP biocompatible matrix was used to produce the composition. The rhPDGF-BB solution was expelled on the β-TCP particles of the biocompatible matrix with a syringe, and the resulting composition was blended and molded in preparation for application at a site of bone fusion in a joint.

EXAMPLE 2

Preparation of a Composition Comprising a Solution of PDGF, a Biocompatible Matrix and a Biocompatible Binder A composition comprising a solution of PDGF and a biocompatible matrix containing a biocompatible binder, collagen, was prepared according to the following procedure.

A pre-weighed block of biocompatible matrix comprising β-TCP and collagen was obtained. The β-TCP comprised β-TCP particles having an average diameter ranging from about 100 μm to about 300 μm. The β-TCP particles were formulated with approximately 20 weight percent soluble bovine collagen binder. A β-TCP/collagen matrix can be commercially obtained from Kensey Nash (Exton, Pa.).

A solution comprising rhPDGF-BB was obtained. rhPDGF-BB is commercially available from Chiron Corporation at a stock concentration of 10 mg/ml (i.e., Lot # QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention, including 1.0 mg/ml.

A ratio of about 3 ml of rhPDGF-BB solution to about 1 g dry weight of the β-TCP/collagen matrix was used to produce the composition. The rhPDGF-BB solution was expelled on the β TCP/collagen matrix with a syringe, and the resulting composition was blended and molded in preparation for application at a site of bone fusion in a joint.

EXAMPLE 3

Method of Performing Arthrodesis of the Foot and/or Ankle

Experimental Design and Overview

The purpose of this prospective, randomized, controlled, multi-center feasibility clinical trial was to evaluate the safety and effectiveness of a composition comprising a PDGF solution disposed in a β-TCP matrix compared to autologous bone graft (ABG) in foot/ankle arthrodetic procedures. The clinical significance of comparing a composition of the present invention to autograft provides for a predictable synthetic alternative to autograft, thus eliminating the morbidity and increased surgical time associated with an additional procedure for harvesting autogenous bone graft, which is only available in limited quantities. Additionally, an adjunctive recombinant growth factor eliminates additional procedures associated with harvesting and preparing bone marrow aspirate or autologous platelet concentrates and increases predictability by eliminating concentration variability associated with such systems. Comparisons were made between the control group (Group I: ABG) and compositions comprising a PDGF solution disposed in a β-TCP matrix (Group II: β-TCP-PDGF, as prepared according to Example 1).

The study enrolled 20 patients presenting with a defect requiring bone fusion in the foot and/or ankle. The fusion space was adequately reduced and stabilized with rigid fixation intra-operatively in order to meet final study eligibility. Subjects were randomized A subject was not enrolled in the study if the surgeon determined on the day of surgery that the bone defect does not meet enrollment criteria or the fusion site cannot be adequately reduced and stabilized according to the protocol.

The treatment groups were: Group I: Standard Rigid Fixation+ABG; and, Group II: Standard Rigid Fixation+β-TCP, with sodium acetate buffer containing 0.3 mg/ml rhPDGF- BB. Subjects in each group were immobilized according to the standard operative and post-operative protocols.

The primary endpoint, mean time to radiographic union (defined as osseous bridging across subchondral surfaces of at least 3 out of 4 bony aspects) was determined based upon plain film radiographs. Computer tomographic (CT) scans provided precise information on union and were taken at periodic intervals as supplemental and confirmatory documentation of healing. Union was determined by independent radiologist(s) assessment based upon the above noted and generally accepted criteria. Clinical and functional assessments consisted of range of motion, time to full weight-bearing (FWB), pain, and patient quality of life/outcomes scores. Also, the length of surgical procedure (i.e. start of first incision to time of closure) was recorded. The schedule for follow-up was followed according to Table 1.

TABLE 1

Study timeline summary

| Visit 1 Screening Visit ↓ | Visit 2 Surgical Visit ↓ | Visit 3 Post Tx Follow Up | Visit 4 Post Tx Follow Up | Visit 5 Post Tx Follow Up | Visit 6 Post Tx Follow Up | Visit 7 Post Tx Follow Up | Visit 8 Post Tx Follow Up | Visit 9 Post Tx Follow Up | Visit 10 Post Tx Follow Up | Visit 11 Post Tx Follow Up |
|---|---|---|---|---|---|---|---|---|---|---|
| Within 12 Days of Surgical Visit | Within 12 Days of Screening | ↓ | ↓ | ↓ | ↓ | ↓ | ↓ | ↓ | ↓ | ↓ |
|  | Day 0 | Day 7-14 | Week 4 ± 7 days | Week 6 ± 7 days | Week 8 ± 7 days | Week 10 ± 7 days | Week 12 ± 7 days | Week 16 ± 14 days | Week 24 ± 14 days | Week 36 ± 14 days |

The primary endpoint was the time to radiographic healing (union) as assessed by plain X-ray films and CT scans. Moreover, secondary radiographic endpoints for evaluating healing in an arthrodetic procedure included callus formation, overall assessment of osseous bridging (CT scans; weeks 6, 12, and 16 only), presence of abnormal bone formation (e.g. heterotopic bone formation, exotosis, hyperplasia), evidence of bone resorption, assessment of β-TCP resoprtion, and hardware complications such as loosening of screws.

In addition to radiographic endpoints, healing in an arthrodetic procedure can be assessed by a variety of clinical and functional endpoints including 24-week union rate, time to full weight bearing, edema/swelling, pain at the surgical site, presence of warmth at the surgical site, evidence of infection and/or ulceration, operative time, incidence of complications or adverse events, and quality of life considerations.

Surgical Protocol

The procedure was performed under either local or general anesthesia, according to co-morbidities and at the discretion of the investigator. Surgical technique was identical in both treatment groups except that Group II had application of the rhPDGF/β-TCP particulate matrix to the site of fusion at the time of rigid fixation, and Group I had ABG applied to the site of fusion at the time of rigid fixation of the fusion site, as specified by the randomization schedule. ABG was harvested either locally or from the iliac crest, as determined by the investigator. In the event a patient was admitted to the hospital after surgery, it would be for reasons separate from the study parameters (e.g., pain control, perioperative complication, medical monitoring, etc.). Any event requiring hospitalization or prolonged hospitalization that was not intended as part of the pre-operative plan was recorded in the case report form and reported to the sponsor.

Operatively, the patient was placed supine with a tourniquet around the thigh. Perioperative prophylactic antibiotics were administered before surgical incision. After routine preparation and draping, standard surgical exposures were employed to gain access to each fusion site. The open surgical approaches employed in this study represent standard medial, lateral, and/or anterior exposures designed to minimize the chance of sensory impairment or neurovascular injury at the time of surgery. The appropriate soft tissues were released as necessary according to standard techniques. This may include tendon release of, for example, the gastrocnemius or Achilles tendon, in the event soft tissue balancing was required to enact more precise anatomic reduction of deformity. The entirety of any involved joint was exposed and denuded to subchondral bone, and the cortices were perforated to augment the subsequent fusion.

The opposing surfaces of the joints to be fused were prepared in standard fashion with the use of small osteotomes, curettes, drilling, a burr, and/or a saw, depending upon the severity of the deformity, the quality of the bone, and the amount of remaining cartilage. Appropriate soft tissues were released as necessary according to standard techniques.

The appropriate joints were subsequently placed in proper alignment and were fused with large fragment screws (3.5 to 7.3 mm, depending upon the size of the patient's foot) to ensure rigid, compressive fixation. The fixation was rigid in order to ensure that the final reduction was maintained during the healing process. No more than four screws were used to ensure rigid fixation. The type of fixation was recorded on the Case Report Form.

A composition of the present invention comprising a PDGF solution disposed in a β-TCP matrix was prepared or ABG was harvested, locally or from the iliac crest, based upon the randomization schedule. Subjects consented to harvesting of local or iliac crest bone graft prior to the surgical procedure, as the subject was blinded to the randomization assignment. For subjects randomized to receive ABG, the harvest site and amount of bone graft was documented on the case report form. Autograft was harvested according to standard bone grafting procedures. The graft material (β-TCP-PDGF or ABG) was packed into the fusion site at the time of fixation such that the graft material was in contact with the entire surface area of the joint to be fused. Approximately 3 to 6 cc of graft material was required for the fusion of each joint. As a general guideline, it was expected that 9 cc would be used for the triple arthrodesis, 6 cc for the subtalar and ankle fusions, and 3 cc for the talonavicular and calcaneocuboid fusions. Those patients randomized to receive ABG undergo an additional surgical incision separate from those required to perform the fusion procedure in the foot/ankle, and those randomized to receive β-TCP-PDGF did not require such additional surgery. The inherent risks and potential benefits of these different approaches were outlined in the surgical consent form.

For multiple fusion procedures, such as triple arthrodesis or talonavicular fusion, an individual (single) joint was defined by the investigator according to defined parameters as the primary fusion site for the purpose of the statistical analysis. Healing/union was assessed collectively for all joints involved as a unit. All involved joint fusions were treated according to the randomization schedule.

Following final fixation of the deformity, additional graft material was placed around the fusion site to maximize graft exposure in order to facilitate osseointegration into the fusion space. Care was taken to ensure that graft material was contained within the fusion space. Once the β-TCP-PDGF or ABG was added in its entirety to the construct, careful layered periosteal and overlying soft tissue closure was performed to Following the first two weeks in a splint, all patients were placed in a short leg cast which was serially changed as necessary for proper fitting and integrity over the course of their ensuing patient follow-up visits for the subsequent 10 weeks. Any deviations from protocol were recorded.

Patients remained non weight-bearing for the first 6 weeks post-operatively, after which progressive, partial weight-bearing (PWB) began. At 6 weeks post-operatively, patients began formal physical therapy to help with their progressive weight-bearing (e.g. gait training, edema control, range of motion of unfused joints, scar mobilization). At 12 weeks, the patients were taken out of their cast and placed into a regular walking shoe with the use of an ankle/hindfoot brace for transitional immobilization. The time of radiographic healing (as assessed by the investigator) and release to full weight-bearing was documented by the investigator. The independent radiologist(s) performed a separate and independent assessment of healing. The frequency and nature of radiographic and functional assessments were provided in Table 2.

TABLE 2

Frequency of Radiographic and Functional Assessments

| | | Radiographic Parameters | | | Functional Assessments | | | |
|---|---|---|---|---|---|---|---|---|
| | Event | Quantitative Radiograph Parameters | Semi-Quantitative Radiograph Parameters | Verify Reduction | Range of Motion | Clinical Eval. | Pain | QOL |
| Periop. Management | Prior to Treatment | X | X | | | X | | X |
| | After Stabilization | | | X | | | | |
| | During Implementation | | | X | | | | |
| | Post Reduction/Implantation Prior to Fixation | | | X | | | | |
| | Immediately Post-Fixation | X | X | | | X | X | |
| Management of Injured Area | Day 7-14 | X | X | | | X | X | |
| | Week 4 | X | X | | | | X | |
| | Week 6 | X | X | | X | X | X | X |
| | Week 8 | X | X | | | X** | X | |
| | Week 10 | X | X | | | X** | X | |
| | Week 12 | X* | X | | X | X | X | X |
| | Week 16 | X* | X | | | | X | |
| | Week 24 | X | X | | X | X | X | X |
| | Week 36 | X | X | | X | X | X | X |

*Confirmatory CT scan taken at Weeks 6, 12 and 16 (if union is not achieved by Week 12).
**Clinical evaluations at Wk 8 and 10 are not required if clinical healing was established by Week 6.

enclose and contain this graft and minimize any risk of washout or subperiosteal resorption, exostosis, and ulceration at the surgical site.

The tourniquet was subsequently deflated, hemostasis carefully maintained, and finally the remainder of the wounds were closed in layers. An ankle block using 0.5% marcaine and 1% lidocaine was administered thereafter to aid in post-operative pain control, and the patient was then placed in a sterile compressive dressing and posterior splint in neutral alignment, awakened from anesthesia, and thereafter discharged to the recovery room.

Follow-Up Evaluation

Subjects were seen for post-operative evaluations at days 7-14 and weeks 4, 6, 8, 10, 12 (+/−1 days), 16, 24, and 36 (+/−14 days) post surgery (Tx), as provided in Table 1. Routine evaluations and procedures were performed during the follow-up period. Post-operatively, the foot or ankle was immobilized in a posterior splint for one to two weeks, at which point each was seen for a first post-operative visit for suture removal and application of a short leg cast (SLC).

Pain to be assessed at the time of hospital discharge, in addition to the noted study visits.

Results

Assessment of computerized tomography (CT) scans of joint fusion sites by an independent reviewer blinded to the treatment groups indicated that at 6 weeks 39% of the patients in Group II receiving the composition comprising rhPDGF-BB incorporated in a β-TCP matrix exhibited osseous bridging of greater than 50% in comparison to 34% of autograft patients. Moreover, at 12 weeks, 63% of patients in Group II exhibited osseous bridging of greater than 50% at joint fusion sites in comparison with 50% of the patients in Group I.

In the clinical evaluations (physician scored AOFAS evaluation) at the six week time point, patients of Group II displayed an average score of 56.2 while patients of Group I displayed an average score of 52.3. The higher score of Group II indicated improved function of the treated joint areas. Additionally, in the patient scored pain assessment (VAS assessment), patients of Group II demonstrated an average score of 16.3, and patients of Group I demonstrated an average score of 26.1 at six weeks. The lower score of patients of Group II indicated a more favorable outcome of the arthrodetic procedure in relation to patient quality of life. Furthermore, patients of Group II receiving the β-TCP+rhPDGF-BB composition did not display any ectopic bone formation or adverse effects on surrounding or distant soft tissues.

EXAMPLE 4

Partial Arthrodesis of the Carpus in Dogs

Experimental Design and Overview

This study evaluated the safety and effectiveness of a composition comprising a solution comprising 0.3 mg/ml PDGF disposed in a β-TCP matrix with or without a collagen binder compared to autologous bone graft in partial arthrodesis of the carpus in dogs. The clinical significance of comparing a composition of the present invention to autograft provides for a predictable synthetic alternative to autograft, thus eliminating the morbidity and increased surgical time associated with an additional procedure for harvesting autogenous bone graft which is only available in limited quantities.

The study enrolled 30 dogs which underwent partial arthrodesis of the carpus. The treatment groups were:
Group I: Autograft (10 dogs)
1. Autograft+rhPDGF-BB (Side A)
2. Autograft only (Side B)
Group II: Particulate β-tricalcium phosphate (β-TCP) (10 dogs)
1. β-TCP+rhPDGF-BB (Side A)
2. β-TCP only (side B)
Particle sizes of the β-TCP ranged from about 250 μm to about 1 mm. The composition was made in a manner similar to that outlined in Example 1.
Group III: β-tricalcium phosphate and collagen binder (β-TCP/collagen) (10 dogs)
1. β-TCP/collagen+rhPDGF-BB (Side A)
2. β-TCP/collagen only (side B)
Particle sizes of the β-TCP ranged from about 100 μm to about 300 μm, and the (β-TCP/collagen material comprised 20 weight percent Type I collagen.
Animals Thirty (30) dogs were acquired from Louisiana State University (LSU) Veterinary School of Medicine and delivered to the University of Iowa Office of Animal Resources (OAR). Each animal received a thorough examination and all health records were transferred to the OAR. All dogs were in good health and underwent a 14 day quarantine period prior to study initiation.
Surgical Protocol Each animal underwent bilateral surgeries with one leg treated with the autograft, (β-TCP, or β-TCP/collagen alone and the opposite side treated with the autograft+rh-PDGF-BB, β-TCP+rh-PDGF-BB, or β-TCP/collagen+rh-PDGF-BB. The side for each treatment was randomized for each animal.

Food and water were withheld from the animals 18 hours prior to surgery. Each animal was brought to the operating room (OR) and Thiopental (20-25 mg/kg IV) was given slowly in the jugular vein until the animal was sedated. A 9 mm intubation tube was inserted for inhalation anesthesia (Isoflurane was delivered in $O_2$ at a rate of 2% and was utilized throughout the procedure). An 18 g catheter was inserted in the femoral vein and lactated ringers solution was administered at a rate of 10 ml/kg/hr. Cefazolin (20 mg/kg IV) was also administered. The animal's forelimbs were clipped of all hair and, if the animal was in the autograft group, a 10×10 inch area above the dog's iliac crest was shaved of all hair.

The animal was placed on the operating room table in the prone position, and both forelimbs and hips were surgically prepped with povidone solution. The animal was then draped with surgical drapes.
Autograft Harvest A 5 cm incision was made over both hips of the animal, and the fascia was incised down to the crest and dissected with a freer. Rongeurs were used to obtain 1.5 cc of corticocancellous autograft from both iliac crests. The fascia was closed with 2.0 Vicryl in a running stitch. The skin was closed in the same routine manner
Forelimbs A 5 cm midline dorsal incision was made through the skin just below the cephalic and accessory cephalic veins and extended distally for 5 cm. The deep antebrachial fascia was incised midway between the extensor carpi radialis tendon and the common digital extensor and retracted with a self retaining retractor. A round 2 mm high speed burr was used to denude the joint surfaces of the distal radial carpal, proximal and distal surfaces of the $3^{rd}$ carpal and the proximal surface of the $3^{rd}$ metacarpal. The joint was irrigated with 10 cc of normal saline. Approximately 1 cc of graft material was placed above and below the $3^{rd}$ carpal bone in the joint space.

A 2-T-3 T-plate from Synthes Ltd. of West Chester, Pa. was placed over the joint and a 2 mm drill bit was used to drill two holes in the radial carpal bone as distally as possible to ensure normal movement of the antebrachiocarpal joint. Two 2.7 mm self tapping screws, each 18 mm in length, were placed in the radial carpal to secure the plate. Additional holes were drilled through the $3^{rd}$ metacarpal and $3^{rd}$ carpal bone. Two 2.7 mm self tapping screws were placed in the metacarpal and one in the carpal. The deep and superficial fascial layers were closed with a running stitch of VICRYL® from Johnson and Johnson. The skin was closed in the same routine manner.

The dogs' limbs were cleaned of all dried blood and povidone solution and wrapped in 2 inch soft roll and 2 inch stockinet. Each limb was then wrapped with 3 layers of 2 inch fiberglass casting tape for immobilization. Casts were worn for at least 8 weeks.

Following the surgical procedure, the animal was placed in a recovery pen. Two Fentanyl patches, one 50 μg/hr and one 25 μg/hr were placed on the dogs neck. Flunixin (1 mg/kg) was given subcutaneously. The animal was allowed to wake up and bear weight on the forelimbs.

Each animal was evaluated for signs of pain, infection, and eating habits. Appropriate analgesics were administered throughout the study in accordance with IACUC approval. Casts were changed at least once a week. 21 of the 30 dogs were humanely sacrificed at 5 weeks post operatively. The remaining dogs were humanely sacrificed at 12 weeks post operatively.
Evaluation
Radiography Standard anteroposterior (AP) x-rays were taken at weekly intervals of each animal to assess fixation and to assess new bone formation and fusion of bones bridging the treated joints.
Calcified Histology Specimen limbs from each group were immersed in 10% formalin for one week, rinsed in water for 24 hours, and subsequently immersed in 70% ethanol. Dehydration was accomplished with an ascending series of alcohols starting from 80% and progressing serially to 90%, 95%, and 100%.

Alcohol was cleared with 100% acetone. Each specimen was embedded in Spurrs plastic for calcified histology.

Serial anterior-posterior sections were ground with 1000, 1200, and 2000 grit grinding discs, polished with 2400 grit polishing paper, and stained with hematoxylin and eosin. A board certified veterinary patholigist examined the histological responses of Groups I, II, and III. Bone fusion at treated joints measured as a function of trabecular bone formation across the joint.

Clinical Assessment—Palpation

Palpation at 5 and 12 weeks was used to qualitatively assess joint fusion. One examiner independently determined the existence of joint fusion across all three treatment Groups. The examiner was blinded to the treatment Groups. Soft tissues were removed from the specimens, and each joint was palpated. The radial carpal and $3^{rd}$ carpal were held, and the bones were stressed to determine the existence of any movement (e.g. fusion across the joint). The same procedure was used for the $3^{rd}$ carpal and $3^{rd}$ metacarpal joint. Results were recorded as "fused" or "not fused."

Results

Thirty (30) dogs entered the study with 28 of the 30 progressing to the terminal stage. Two animals were prospectively omitted. While radiographs were taken weekly as provided herein, visualization of the joint space was not possible until the T-plate was removed. T-plate removal was conducted following humane sacrifice of the animals. As a result, the data presented herein corresponds to post-sacrifice radiographs. The radiographic results detailing osseous bridging are summarized in Tables 3 and 4.

TABLE 3

Five Week Radiographic Osseous Bridging

| Group/Composition | Radial Carpal/ $3^{rd}$ Carpal (Percent of Joints Having Osseous Bridging) | $3^{rd}$ Carpal/$3^{rd}$ Metacarpal (Percent of Joints Having Osseous Bridging) |
|---|---|---|
| I. Autograft only | 33 | 67 |
| I. Autograft + rhPDGF-BB | 33 | 100 |
| II. β-TCP only | 29 | 57 |
| II. β-TCP + rhPDGF-BB | 43 | 29 |
| III. β-TCP/collagen | 50 | 83 |
| III. β-TCP/collagen + rhPDGF-BB | 50 | 83 |

TABLE 4

Twelve Week Radiographic Osseous Bridging

| Group/Composition | Radial Carpal/ $3^{rd}$ Carpal (Percent of Joints Having Fusion) | $3^{rd}$ Carpal/$3^{rd}$ Metacarpal (Percent of Joints Having Fusion) |
|---|---|---|
| I. Autograft only | 66 | 33 |
| I. Autograft + rhPDGF-BB | 100 | 100 |
| II. β-TCP only | 66 | 66 |
| II. β-TCP + rhPDGF-BB | 66 | 38 |
| III. β-TCP/collagen | 66 | 66 |
| III. β-TCP/collagen + rhPDGF-RR | 100 | 100 |

The results of the palpation assessments are present in Tables 5 and 6.

TABLE 5

Five Week Palpation Osseous Bridging Assessment

| Group/Composition | Radial Carpal/ $3^{rd}$ Carpal (Percent of Joints Having Osseous Bridging) | $3^{rd}$ Carpal/ $3^{rd}$ Metacarpal (Percent of Joints Having Osseous Bridging) |
|---|---|---|
| I. Autograft only | 50 | 17 |
| I. Autograft + rhPDGF-BB | 67 | 33 |
| II. β-TCP only | 14 | 43 |
| II. β-TCP + rhPDGF-BB | 57 | 43 |
| III. β-TCP/collagen | 50 | 33 |
| III. β-TCP/collagen + rhPDGF-BB | 50 | 67 |

TABLE 6

Twelve Week Palpation Osseous Bridging Assessment

| Group/Composition | Radial Carpal/ $3^{rd}$ Carpal (Percent of Joints Having Osseous Bridging) | $3^{rd}$ Carpal/ $3^{rd}$ Metacarpal (Percent of Joints Having Osseous Bridging) |
|---|---|---|
| I. Autograft only | 66 | 66 |
| I. Autograft + rhPDGF-BB | 100 | 100 |
| II. β-TCP only | 66 | 66 |
| II. β-TCP + rhPDGF-BB | 66 | 66 |
| III. β-TCP/collagen | 66 | 66 |
| III. β-TCP/collagen + rhPDGF-BB | 100 | 100 |

As demonstrated by the foregoing data, joints treated with compositions comprising rhPDGF-BB displayed enhanced osseous bridging and fusion. Moreover, β-TCP compositions comprising rhPDGF-BB demonstrated osseous bridging and joint fusion results comparable to autograft compositions, thereby precluding the necessity to harvest autograft for arthrodetic procedures. Eliminating autograft harvesting from arthrodetic procedures reduces patient pain and discomfort while facilitating the joint fusion process.

Moreover, the histological results of the present study confirmed normal bone formation processes with no ectopic bone formation or adverse effects on surrounding or distant soft tissues.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method of performing an arthrodetic procedure on a subject comprising:
   a step of applying to a site of desired bone fusion in a joint a composition comprising a platelet derived growth factor (PDGF) solution and a biocompatible matrix, wherein the solution is disposed in the biocompatible matrix;
   wherein the biocompatible matrix comprises either a bone scaffolding material or comprises a bone scaffolding material and a biocompatible binder;

wherein the bone scaffolding material comprises β-tricalcium phosphate (β-TCP) having interconnected pores; and wherein the method promotes fusion of bones of the joint.

2. The method of claim 1, wherein the biocompatible binder is selected from the group consisting of: collagen, polysaccharides, carbohydrates, poly(α-hydroxy acids), poly(lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, alginic acid, arabic gum, guar gum, xantham gum, gelatin, chitin, chitosan, chitosan acetate, chitosan lactate, chondroitin sulfate, lecithin, N,O-carboxymethyl chitosan, phosphatidylcholine derivatives, a dextran, fibrin glue, glycerol, hyaluronic acid, sodium hyaluronate, a cellulose, a glucosamine, a proteoglycan, a starch, lactic acid, a pluronic acid, sodium glycerophosphate, glycogen, a keratin, silk, and copolymers and mixtures thereof.

3. The method of claim 2, wherein the biocompatible binder comprises collagen.

4. The method of claim 1, wherein the PDGF concentration is about 0.1 to about 1.0 mg/ml.

5. The method of claim 1, wherein the PDGF concentration is about 0.3 mg/ml.

6. The method of claim 1, wherein the PDGF comprises PDGF-BB.

7. The method of claim 1, wherein the PDGF comprises recombinant human PDGF-BB (rhPDGF-BB).

8. The method of claim 1, wherein the rhPDGF-BB comprises at least 65% intact rhPDGF-BB.

9. The method of claim 1, wherein the bone scaffolding material comprises particles having an average diameter of: from about 100 microns to about 5000 microns, from about 1000 microns to about 2000 microns; or from about 100 microns to about 300 microns.

10. The method of claim 1, wherein the bone scaffolding material comprises a porosity greater than about 50%.

11. The method of claim 1, wherein the bone scaffolding material comprises a porosity greater than about 90%.

12. The method of claim 1, wherein the bone scaffolding material comprises macroporosity.

13. The method of claim 1, wherein the bone scaffolding material comprises a porosity that facilitates osteoinduction and osteoconduction into the biocompatible matrix.

14. The method of claim 1, wherein the arthrodetic procedure further comprises the additional steps of aligning the bones to be fused and inserting at least one screw into at least one bone or of the joint.

15. The method of claim 1, wherein the arthrodetic procedure comprises an arthrodetic procedure of the foot and ankle.

16. The method of claim 1, wherein the arthrodetic procedure comprises a subtalar arthrodesis, a talonavicular arthrodesis, a triple arthrodesis, or an ankle arthrodesis.

17. The method of claim 1, wherein the site of the desired bone fusion is selected from the group consisting of a subtalar joint, a talonavicular joint, a calcaneocuboid joint, and an ankle joint.

18. The method of claim 1, wherein the arthrodetic procedure comprises a spinal arthrodetic procedure.

19. The method of claim 1, wherein the biocompatible matrix consists of the bone scaffolding material and collagen.

20. The method of claim 19, wherein the PDGF concentration is about 0.1 to about 1.0 mg/ml.

21. The method of claim 19, wherein the PDGF concentration is about 0.3 mg/ml.

22. The method of claim 19, wherein the PDGF comprises PDGF-BB.

23. The method of claim 19, wherein the PDGF comprises recombinant human PDGF-BB (rhPDGF-BB).

24. The method of claim 19, wherein the rhPDGF-BB comprises at least 65% intact rhPDGF-BB.

25. The method of claim 19, wherein the bone scaffolding material consists of particles having an average diameter of: from about 100 microns to about 5000 microns; from about 100 microns to about 300 microns; or from about 1000 microns to about 2000 microns.

26. The method of claim 19, wherein the bone scaffolding material comprises a porosity greater than about 50%.

27. The method of claim 19, wherein the bone scaffolding material comprises a porosity greater than about 90%.

28. The method of claim 19, wherein the bone scaffolding material comprises macroporosity.

29. The method of claim 19, wherein the bone scaffolding material comprises a porosity that facilitates osteoinduction and osteoconduction into the biocompatible matrix.

30. The method of claim 19, wherein the collagen comprises Type I collagen.

31. The method of claim 19, where the ratio of collagen: β-tricalcium phosphate is about 20:80 by weight.

32. The method of claim 1, wherein the bone scaffolding material consists of particles having an average diameter from about 100 to about 5000 microns, wherein the PDGF concentration is about 0.1 to about 1.0 mg/ml, and wherein the PDGF comprises rhPDGF-BB.

33. The method of claim 32, wherein the β-tricalcium phosphate comprises a porosity greater than about 50%.

34. The method of claim 32, wherein the PDGF concentration is about 0.3 mg/ml.

35. The method of claim 32, wherein the arthrodetic procedure further comprises the additional steps of aligning the bones to be fused and inserting at least one screw into at least one bone of the joint.

36. The method of claim 32, wherein the arthrodetic procedure comprises an arthrodetic procedure of the foot and ankle.

37. The method of claim 36, wherein the arthrodetic procedure comprises a subtalar arthrodesis, a talonavicular arthrodesis, a triple arthrodesis, or an ankle arthrodesis.

38. The method of claim 32, wherein the site of the desired bone fusion is selected from the group consisting of a subtalar joint, a talonavicular joint, a calcaneocuboid joint, and an ankle joint.

39. The method of claim 32, wherein the arthrodetic procedure comprises a spinal arthrodetic procedure.

40. The method of claim 1, wherein the bone scaffolding material consists of particles having an average diameter from about 100 to about 300 microns, wherein the PDGF concentration is about 0.1 to about 1.0 mg/ml, and wherein the PDGF comprises rhPDGF-BB.

41. The method of claim 40, wherein the β-tricalcium phosphate comprises a porosity greater than about 50%.

42. The method of claim 40, wherein the PDGF concentration is about 0.3 mg/ml.

43. The method of claim 40, wherein the arthrodetic procedure further comprises the additional steps of aligning the bones to be fused and inserting at least one screw into at least one bone of the joint.

44. The method of claim 40, wherein the arthrodetic procedure comprises a spinal arthrodetic procedure.

45. The method of claim 1, wherein the bone scaffolding material consists of particles having an average diameter from about 1000 to about 2000 microns, wherein the PDGF concentration is about 0.1 to about 1.0 mg/ml, and wherein the PDGF comprises rhPDGF-BB.

46. The method of claim 45, wherein the @-tricalcium phosphate comprises a porosity greater than about 50%.

47. The method of claim 45, wherein the PDGF concentration is about 0.3 mg/ml.

48. The method of claim 45, wherein the arthrodetic procedure further comprises the additional steps of aligning the bones to be fused and inserting at least one screw into at least one bone of the joint.

49. The method of claim 45, wherein the arthrodetic procedure comprises a spinal arthrodetic procedure.

50. The method of claim 1, wherein the bone scaffolding material consists of particles having an average diameter from about 250 to about 1000 microns, wherein the PDGF concentration is about 0.1 to about 1.0 mg/ml, and wherein the PDGF comprises rhPDGF-BB.

51. The method of claim 50, wherein the arthrodetic procedure further comprises the additional steps of aligning the bones to be fused and inserting at least one screw into at least one bone of the joint.

52. The method of claim 50, wherein the arthrodetic procedure comprises a spinal arthrodetic procedure.

53. The method of claim 1, wherein the composition is flowable, moldable, and/or extrudable.

54. The method of claim 1, wherein the composition is flowable, moldable, and/or injectable.

55. The method of claim 1, wherein the composition is moldable, extrudable, and/or injectable.

\* \* \* \* \*